United States Patent [19]

Kurasawa

[11] Patent Number: 4,996,055
[45] Date of Patent: Feb. 26, 1991

[54] DEODORIZED BACTERIA COMPOSITION

[75] Inventor: Morio Kurasawa, Tokyo, Japan

[73] Assignee: Kurasawa Optical Industry Co., Ltd., Tokyo, Japan

[21] Appl. No.: 341,443

[22] Filed: Apr. 21, 1989

[51] Int. Cl.⁵ .................. A61K 39/02; A23K 00/00
[52] U.S. Cl. ............................ 424/442; 424/76.8; 424/76.6; 424/92; 435/839; 435/842
[58] Field of Search ............... 424/76.6, 76.8, 442, 424/92; 435/839, 842

[56] References Cited

U.S. PATENT DOCUMENTS 4,321,141 3/1982 Messing .................. 435/176
4,808,417 2/1989 Masuda .................... 426/53
4,879,238 11/1989 Hata ...................... 424/76.6
4,919,936 4/1990 Iwanami et al. ........... 424/442

Primary Examiner—Merrell C. Cashion, Jr.
Assistant Examiner—James M. Spear
Attorney, Agent, or Firm—Griffin, Branigan & Butler

[57] ABSTRACT

A deodorant has the genus butyric acid bacteria and the genus *Bacillus subtilis* as effective components and is used for deodorizing the excrement of various animals and other sources of foul odors. The combined use of the genus butyric acid bacteria and the genus *Bacillus subtilis* makes it possible to deodorize the sources of foul odors by decomposing hydrogen sulfide, ammonia, mercaptan, etc., contained in the sources of the foul odors.

9 Claims, No Drawings

DEODORIZED BACTERIA COMPOSITION

BACKGROUND OF THE INVENTION

The present invention relates to a bacterial deodorizer which is used for deodorizing the excrement of animals by being mixed into the feed of domestic animals such as cattle, horses, pigs and chickens and various other animals such as dogs, cats, rabbits, foxes, raccoon dogs, guinea pigs, mice, minks, martens, squirrels, and hamsters, or which is used for deodorizing the excrement of the aforementioned various animals, fish, and garbage, or for deodorizing the sources of foul odors such as raw sewage treatment plants, waste incineration plants, aeration tanks used in sewage treatment tanks, and toilets.

Gut florae (microflorae) that live in the digestive tracts of large animals, such as domestic animals, exhibit nutritional functions such as the metabolism of nutrients and the synthesis of vitamins, as well as the prevention of contagion or infection from diseases, thereby playing an important role in the growth of animals and in the maintenance of their health. A disorder in the proportions of the gut florae manifests itself as diarrhea. Bacteria have been used as remedies for diarrhea or the like for a long time. Included among the bacterial agents used as such remedies are *Bacillus toyoi, Clostridium butyricum miyairi, Bacillus coagulans, Bacillus subtilis var.Natto, Bifidobacterium thermophilum, Streptococcus faecalis,* and the like. However, these bacterial agents are conventionally employed singly, and they do not exhibit a noticeable effect of deodorizing feces or the like.

Included among the known conventional deodorizers are one using tetracoccus, one using Zeolite (brand name) whose principal components are $SiO_2$, $Al_2O_3$, $CaO$, $Na_2O$, $K_2O.H_2O$, and one which has active humic acid as a principal component and to which calcium carbonate is added.

With the aforementioned conventional deodorizers, however, the one using tetracoccus displays a substantial deodorizing effect with respect to excrement, but the other deodorizers exhibit substantially no deodorizing effect with respect to excrement.

The feces and urine of animals, particularly the multiplicity of domestic animals bred in barns, give off foul odors, and not only constitute a public nuisance but also cause water pollution, so that it cannot be discharged as sewage for treatment. In addition, cleaning work at the barn involves discomfort due to the foul odors of the entire barn. If the feces and urine are left as they are, the barn becomes unsanitary, and may cause the domestic animals to cough, become restless and lose their appetite, resulting in bad growth. In addition, when feces is used as manure, a place for drying is required. With the conventional art, however, these problems cannot be solved.

SUMMARY OF THE INVENTION

Accordingly, an object of the present invention is to provide a deodorant which can be used for deodorizing the feces and urine excreted by animals by being mixed into their feed so as to remove the cause for a public nuisance such as foul odors, improve the growth of the animals, and facilitate transportation thereof for drying, and which can also be used for deodorizing various sources of foul odors such as refuse of fish, thereby overcoming the above-described drawbacks of the prior art.

To this end, according to the present invention, there is provided a deodorant having the genus butyric acid bacteria and the genus *Bacillus subtilis* as effective components.

DETAILED DESCRIPTION OF THE PREFERRED EMBODIMENTS

A deodorant in accordance with the present invention has the genus butyric acid bacteria and the genus *Bacillus subtilis* as effective components.

The aforementioned the genus butyric acid bacteria and the genus *Bacillus subtilis* can be mixed with either rice bran or wheat bran or both.

The amount of the aforementioned the genus butyric acid bacteria and the genus *Bacillus subtilis* mixed with rice bran and/or wheat bran is preferably from 0.1 to 10% by weight. In other words, if the amount is less than 0.1% with respect to the rice bran and/or wheat bran, the deodorizing effect is deteriorated, while if the amount is more than 10%, it is impossible to obtain an advantageous effect and the cost becomes high.

*Clostridium butyricum miyairi,* butyric acid bacteria, etc., can be used as the aforementioned genus butyric acid bacteria, while *Bacillus subtilis var.Natto, Bacillus subtilis,* etc. can be used as the genus *Bacillus subtilis.* The genus butyric acid bacteria and the genus *Bacillus subtilis* alone can be fed directly to the animals. In addition, the genus butyric acid bacteria and the genus *Bacillus subtilis* alone can be used directly in the air or in water, or can be mixed with alcohol or water and used as a spray-type deodorant so as to deodorize sources of foul odors.

In addition, a deodorant which is obtained by mixing the genus butyric acid bacteria and the genus *Bacillus subtilis* with rice bran and/or wheat bran and allowing it to undergo incubation under conditions of constant temperature and humidity may be administered by being added to the feed of animals, or it may be added and mixed with the sources of the foul odors. As described above, since either rice bran or wheat bran or both are used, the bran serves as a carbon source for the growth of the genus butyric acid bacteria and the genus *Bacillus subtilis,* and gaps suitable for the ventilation and incubation of the genus butyric acid bacteria and the genus *Bacillus subtilis* can thereby be provided.

In accordance with the present invention, by the combined use of the genus butyric acid bacteria and the genus *Bacillus subtilis,* it is possible to deodorize sources of foul odors by decomposing hydrogen sulfide, ammonia, mercaptan, etc. contained in the source of the foul odors. For instance, in cases where the deodorant is mixed into the feed of an animal, since the feed is fermented in the stomach, the source of a foul odor can be deodorized in the stomach efficiently, thereby making it possible to deodorize the excreted feces and urine. If the genus butyric acid bacteria and the genus *Bacillus subtilis* are used independently, or the genus butyric acid bacteria or the genus *Bacillus subtilis* are used jointly with other bacteria, no noticeable deodorizing effect can be obtained, but a noticeable deodorizing effect is exhibited by the combined use of the genus butyric acid bacteria and the genus *Bacillus subtilis.* Therefore, it is conjectured that the genus butyric acid bacteria and the genus *Bacillus subtilis* produce a synergistic effect. In addition, if the feces and urine of animals are deodorized as described above, it is possible to prevent the public nuisance caused by foul odor and water pollution and maintain the entire barn or a house in a clean state. Particularly in the case of domestic animals bred in barns, it is possible to accelerate their growth, and the feces which is produced in large amounts can be utilized effectively as manure or the like. In addition, various other sources of foul odors can be deodorized. Hence, the deodorant in accordance with the present invention is effective in preventing public nuisances and water pollution.

EXAMPLES

Hereafter, examples of the present invention will be described.

*Clostridium butyricum miyairi* which belongs to the genus butyric acid bacteria and *Bacillus subtilis var.-Natto* which belongs to the genus *Bacillus subtilis* were mixed at a ratio of 1 to 1 at the weight percent shown in the following Examples 1 to 26 with respect to a mixture of rice bran and wheat bran, and were incubated under conditions of constant temperature and humidity.

|  | Rice Bran | Wheat Bran | *Clostridium butyricum* miyairi and *Bacillus subtilis* var. Natto |
|---|---|---|---|
| Example 1 | 10.0 | 89.9 | 0.1 |
| Example 2 | 20.0 | 79.9 | 0.1 |
| Example 3 | 30.0 | 69.9 | 0.1 |
| Example 4 | 40.0 | 59.9 | 0.1 |
| Example 5 | 50.0 | 49.9 | 0.1 |
| Example 6 | 60.0 | 39.9 | 0.1 |
| Example 7 | 70.0 | 29.9 | 0.1 |
| Example 8 | 80.0 | 19.9 | 0.1 |
| Example 9 | 90.0 | 9.9 | 0.1 |
| Example 10 | 50.0 | 49.8 | 0.2 |
| Example 11 | 50.0 | 49.7 | 0.3 |
| Example 12 | 50.0 | 49.6 | 0.4 |
| Example 13 | 50.0 | 49.4 | 0.6 |
| Example 14 | 50.0 | 49.2 | 0.8 |
| Example 15 | 50.0 | 49.0 | 1.0 |
| Example 16 | 50.0 | 48.5 | 1.5 |
| Example 17 | 50.0 | 48.0 | 2.0 |
| Example 18 | 50.0 | 47.5 | 2.5 |
| Example 19 | 50.0 | 47.0 | 3.0 |
| Example 20 | 50.0 | 46.0 | 4.0 |
| Example 21 | 50.0 | 45.0 | 5.0 |
| Example 22 | 50.0 | 44.0 | 6.0 |
| Example 23 | 50.0 | 43.0 | 7.0 |
| Example 24 | 50.0 | 42.0 | 8.0 |
| Example 25 | 50.0 | 41.0 | 9.0 |
| Example 26 | 50.0 | 40.0 | 10.0 |

The deodorants of the aforementioned Examples 1 t 26 were added to refuse of fish and were mixed therewith. When the presence of odors was checked after a lapse of one hour, it was confirmed that all the samples had been deodorized substantially perfectly. In addition, the deodorants of the aforementioned Examples 1 to 26 were added to the refuse of fish and were mixed therewith, and the presence of odors was confirmed after lapses of one day, two days, three days and five days. Refuse of fish to which the deodorizers were not added was prepared as comparative examples. In the case of the refuse of fish to which the deodorants were not added, bloody water was separated, and foul odors were issued. However, in the case of the refuse of fish to which the deodorants in accordance with Examples of the present invention were added, no foul odors were issued, and the fermentation had progressed and the refuse was dry. The situation was such that the refuse, excluding the bones, could be used as raw material for feed as it was.

In addition, as a result of administering 20 g per day of the aforementioned Examples 7, 15, and 21 to each pig by adding them to their feed, it was possible to not only deodorize the excreted feces and urine but also eliminate the entire foul odors of the entire barn after a lapse of 20 days. In addition, since the feces and urine were deodorized, the pigs ceased to cough and ceased to be restless, and their appetite increased. As compared with the pigs for which the deodorizers were not used, it was possible to accelerate the growth of the pigs by about 20%, thereby making it possible to reduce the period of fatting. Moreover, as compared with the pigs for which the deodorizers were not used, the rate of propagation increased, and the rate of increase was two piglets per pig on average. In addition, since *Clostridium butyricum miyairi* and *Bacillus subtilis var.Natto* are useful in preventing and curing the symptom of microbial substitution which is attributable to a disorder in gut florae, the pigs no longer suffered from diarrhea and white diarrhea. In addition, since the feces can be fermented as described above, the feces can be used adequately as organic manure for such as agricultural use, afforestation use, and horticultural use, and can also be used adequately as a soil conditioning agent.

In addition, as a result of administering 30 g per day of the aforementioned Examples 7, 15 and 21 to each ox by adding them to the feed, it was possible to not only deodorize the excreted feces and urine but also deodorize the entire barn after a lapse of 20 days in the same way as the case where they were administered to pigs. As a result, their growth was accelerated, and although the oxen are conventionally shipped in 18 months, but it was possible to reduce that period of shipment to 15 months. The quality of meat also improved, and the proportions of high-grade and medium-grade meat increased, and the proportion of high-grade meat, in particular, increased by 15 to 20%. In addition, when the cattle were grazed, the feces was naturally turned into manure, and the grass in the vicinity of the area where the feces dropped grew very well, the cattle showed a preference to feed on it.

Furthermore, as a result of administering 2 g per day of the aforementioned Examples 7, 15 and 21 to each chicken by adding them to the feed, it was possible to not only deodorize the excreted feces and urine but also reduce the cholesterol in the yolk of eggs and increase amino acids. In addition, as a result of administering the deodorants by adding them to the feed of broilers, their growth improved, and their meat became softer in terms of meat quality.

As a result of administering the aforementioned Examples 7, 15 and 21 to dogs and cats by adding them to their feed, it was possible to deodorize their excreted feces and urine, and the gloss of their hair improved. This phenomenon in which the gloss of hair is improved was also noted in cases where the deodorants were administered to fur-related animals such as minks, martens, and foxes.

In addition, thanks to the use of the aforementioned Examples, the mortality rate during infancy declined remarkably and was substantially nil for the respective kinds of animals, while their propagation rate increased and they ceased to suffer from diarrhea.

A noticeable deodorizing effect was noted in cases where even very small amounts of *Clostridium butyricum miyairi* and *Bacillus subtilis var.Natto* were used in Examples 1–9. The amounts of *Clostridium butyricum miyairi* and *Bacillus subtilis var.Natto* were increased sharply in Examples 10 to 26. In addition, the genus butyric acid bacteria and the genus *Bacillus subtilis* alone may be used directly in the air or in water so as to deodorize the sources of foul odors. As a result of using the deodorant in accordance with the present invention, a noticeable deodorizing effect was noted, and it was thus found that this deodorant can be used effectively in preventing public nuisances caused by foul odors and water pollution. Incidentally, the ratio between the *Bacillus subtilis var.Natto* and the genus butyric acid bacteria should not be restricted to 1:1 as in the aforementioned examples, and may be selected appropriately, such as 1:2, 1:3, 2:1, and 3:1, etc.

It should be noted that it can be readily conjectured that the same deodorizing effect as that described above could be obtained even if a butyric acid bacteria other than *Clostridium butyricum miyairi* is used and a *Bacillus subtilis* other than *Bacillus subtilis var.Natto* is used.

What is claimed is:

1. A composition for deodorizing animal, fish and bird excrements comprising a deodorizing effective amount of a synergistic combination consisting essentially of at least one butyric acid producing bacteria and at least one bacteria from the genus *Bacillus subtilis* mixed with a carbon containing growth substrate wherein there is 0.1 to 10% by weight of said synergistic combination of bacteria wherein the ratio of the bacteria from the genus *Bacillus Subtilis* to the butyric acid-producing bacteria is between about 1:3 to 3:1.

2. The composition of claim 1 wherein the growth substrate is a carbohydrate.

3. The composition of claim 2 wherein the carbohydrate is a cereal grain component.

4. The composition of claim 3 wherein the grain component is selected from the group consisting of rice bran, wheat bran and mixtures thereof.

5. The composition of claim 1 wherein the butyric acid-producing bacteria is *Clostridium butyricum miyairi*.

6. The composition of claim 5 wherein the *Bacillus subtilis* bacteria is selected from the group consisting of *Bacillus subtilis var. Natto, Bacillus subtilis* and mixtures thereof.

7. The composition of claim 1 in admixture with a feed for animals, fish and birds.

8. The composition of claim 1 wherein the said ratio is between about 1:2 and 2:1.

9. The composition of claim 8 wherein said ratio is 1:1.

* * * * *